United States Patent
Khan et al.

(10) Patent No.: US 10,340,546 B1
(45) Date of Patent: Jul. 2, 2019

(54) SELF-RECHARGEABLE BIO-FUELING MICRO BATTERY WITH A GLUCOSE BURNING CHAMBER

(71) Applicant: Samuel Messinger, Ramot Beit Shemesh Gimmel (IL)

(72) Inventors: Shamsuddin Sultan Khan, Rajshahi (BD); Samuel Messinger, Ramot Beit Shemesh Gimmel (IL)

(73) Assignee: Samuel Messinger, Ramot Beit Shemesh (IL)

( * ) Notice: Subject to any disclaimer, the term of this patent is extended or adjusted under 35 U.S.C. 154(b) by 0 days.

(21) Appl. No.: 16/143,750

(22) Filed: Sep. 27, 2018

(51) Int. Cl.
| | |
|---|---|
| *H01M 8/16* | (2006.01) |
| *H01M 10/44* | (2006.01) |
| *H01M 10/42* | (2006.01) |
| *H01M 8/02* | (2016.01) |
| *A61N 1/378* | (2006.01) |
| *G01S 19/01* | (2010.01) |
| *H04B 1/38* | (2015.01) |

(52) U.S. Cl.
CPC .............. *H01M 8/16* (2013.01); *A61N 1/378* (2013.01); *G01S 19/01* (2013.01); *H01M 10/425* (2013.01); *H01M 10/44* (2013.01); *H04B 1/38* (2013.01)

(58) Field of Classification Search
CPC .... H01M 8/16; H01M 8/0284; H01M 8/0286; H01M 8/0256; H01M 8/0271; H01M 4/90
See application file for complete search history.

(56) References Cited

U.S. PATENT DOCUMENTS

2013/0026969 A1* 1/2013 Kim ...................... A61N 1/3785
320/103
2016/0324449 A1* 11/2016 Gross ................... A61B 5/1459

* cited by examiner

*Primary Examiner* — Karie O'Neill Apicella
(74) *Attorney, Agent, or Firm* — Carrie M. Stroup (57) ABSTRACT

Various embodiments of a biocompatible, self-rechargeable bio-fueling micro battery with a glucose burning chamber, are disclosed herein, to power an implanted medical device. The micro battery comprises a bio-membrane that is configured to diffuse a plurality of bio-fluids across an anode and cathode electrode. The bio-membrane includes: a biocompatible compartment storing at least one of a chemical substance configured to operate a plurality of bio-medical implant devices; one or more bio-fuel compartments (blood, glucose, and/or microbial) configured to store bio-fuels for generating electrolyte and to create a conductive path for electrons emitted by electrodes; and a processor in communication with the biocompatible compartment through plurality of connectors interface with the one or more bio fuel compartments to control the communication between user and the bio medical implant devices. The biofluids comprise a lemon juice, an orange juice, a pineapple juice, and a sour juice; and/or an ingested food.

18 Claims, 7 Drawing Sheets

SELF-RECHARGEABLE BIO-FUELING MICRO BATTERY WITH A GLUCOSE BURNING CHAMBER

TECHNICAL FIELD

The present disclosure generally relates to portable, implantable power equipment. More particularly, the present disclosure relates to an implantable self-rechargeable bio-fueling micro battery with a glucose burning chamber that is able to power another implanted medical device.

BACKGROUND

The number of implantable medical devices has dramatically increased in the field of medicine. Over the last decade, the use of stents, drug eluting stents, pacemakers, defibrillators, ventricular assist devices, glucose infusion pumps and neurostimulators has increased many folds. Some of the above enumerated examples, as well as a number of other implantable and/or non-implantable medical devices, are active devices that require power sources for operation.

The conventional power sources or batteries that are utilized in conjunction with implantable or non-implantable medical devices typically have stringent specifications imposed upon them relative to their physical size and performance. In older generation power sources, batteries that were designed for implantable medical devices were larger batteries, as compared to today's miniature batteries, and with a relatively short useful life. However, with the advent of miniature implantable medical devices for such diverse applications as drug delivery, glucose sensing and monitoring, and neurostimulation, batteries are required that are capable of providing useful power and occupying ever smaller volumes. In addition to small size, a battery that is to be implanted should preferably include a useful life, insignificant self-discharge rates, a high reliability over a long time period, and compatibility with a patient's internal body chemistry. In other words, it should be as biocompatible as possible. Biocompatible coatings and/or encapsulates well known in the art may be utilized to meet this need.

Implantable devices require power source(s) for their functional operation. For example, pacemakers have been widely used to stimulate heart muscles; and lithium batteries within the pacemakers are used to provide power to the pacemaker. Emerging technologies, such as MEMS (MicroElectroMechanical Systems), promise to improve the quality of life for patients that suffer from chronicle diseases. Implantable sensors made by MEMS technology have the advantages of low-cost, small-in-size, easy integration with the controlling integrated circuits (ICs) and low power consumption. However, the size of conventional lithium batteries is large compared to the MEMS-based sensors and post-processing will often be needed to integrate the battery with the sensors.

In the light of the aforementioned discussion, there exists a need of an implantable, self-rechargeable, bio-fueling micro battery that is useable for powering implanted medical devices. The power source of the micro-batteries of the present invention has many applications, such as monitoring and burning excess glucose in the blood. This is especially important for pill and insulin dependent diabetics who rely upon an external device for monitoring their blood sugar levels.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

An exemplary preferred embodiment of the present disclosure is to provide a biocompatible, self-recharging micro battery that is able to be safely and effectively implanted within a human body to power at least one implanted medical device, e.g. one that is co-located with or near the micro battery. The micro battery recharges from a plurality of body fluids, which may include, but is not limited to: blood, glucose, intestinal microbes, consumed juices, and the like; and/or through direct injection of a balloon nipple located on the micro battery.

In an embodiment, the self-rechargeable bio-fueling micro battery, comprises: a bio-membrane configured to diffuse at least one bio-fluid across an anode electrode and a cathode electrode to generate electron follow for recharging the micro battery and/or for supplying power to a connected bio-medical implanted device. The bio-membrane comprises: a biocompatible compartment storing at least one of a chemical substance configured to generate electricity to power the bio-medical implanted device; and one or more biofuel compartments configured to store at least one bio-fuel for generating an electrolyte to create a conductive path for electrons emitted by the anode electrode and the cathode electrode.

In an embodiment, electrodes extend from at least one biofuel compartment(s) into the surrounding tissue into which the micro battery is implanted, wherein the battery may or may not be within a housing comprising holes for the electrodes to extend out of.

Figure 3:
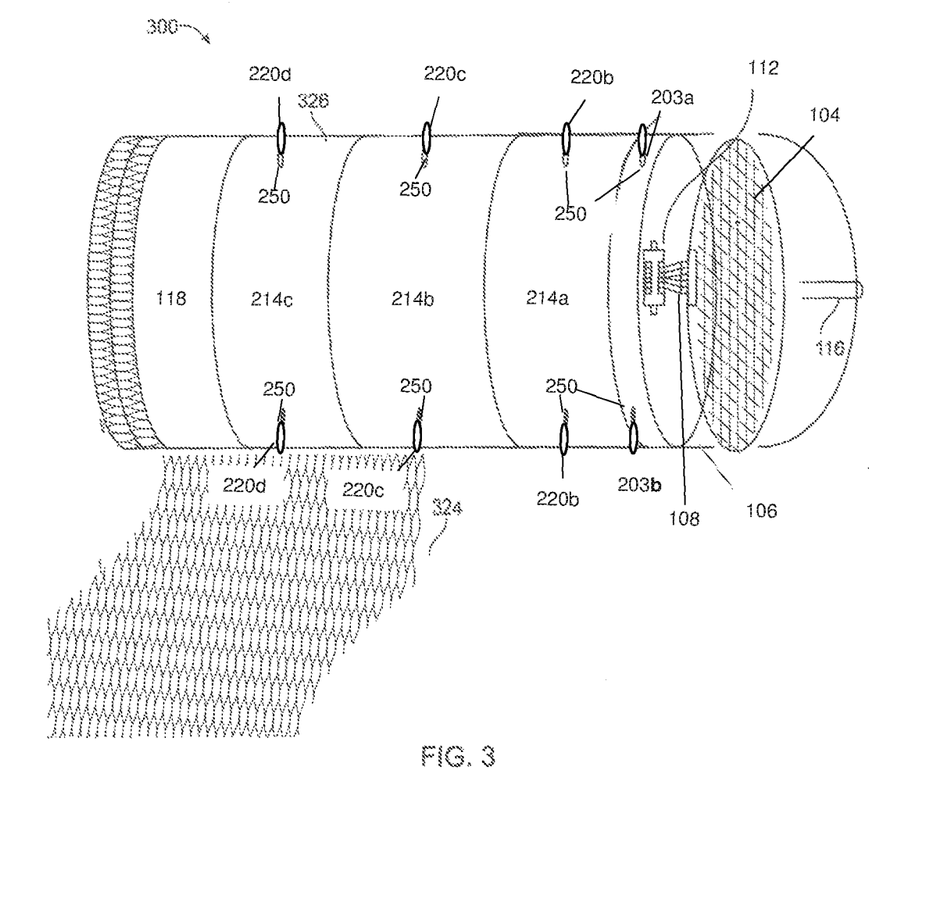
FIG. 3 is a diagram illustrating a closed container housing a the self-rechargeable bio-fueling micro battery, e.g. per FIG. 2, that is implanted in the stomach lining of a human body, wherein the container comprises at least a glucose biofuel compartment, and may further comprise a blood and/or a microbe compartment, and electrodes extending from the container side holes, and a nipple extending from the top end of the container for refilling of the biocompatible compartment.
Figure 4:
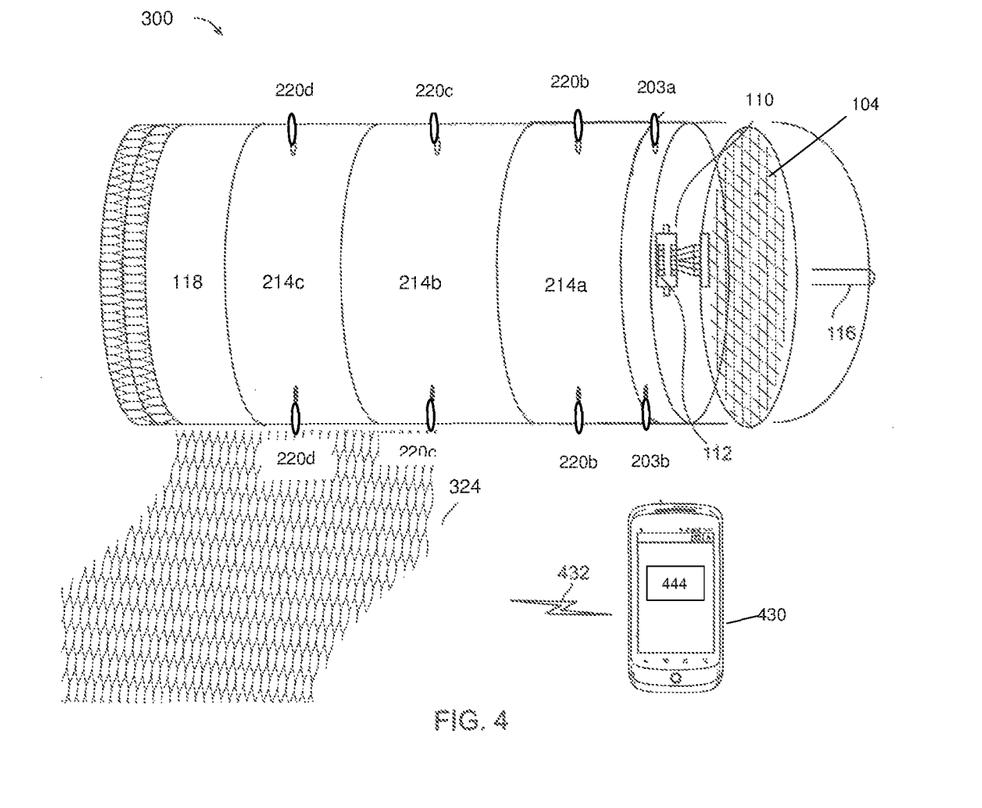
FIG. 4 is a diagram illustrating the container of FIG. 3 and housing the micro-battery of FIG. 2, or part thereof (e.g. one, two, or three bio-fuel compartments) and able to establish a communication between the micro battery and a and electronic computing device comprising a mobile application installed thereon and a network connection between the micro battery processor-transceiver and the computing device.

In another embodiment, electrodes extend from the biofuel compartments and from the biocompatible compartment, and through a micro battery housing into the surrounding tissue (e.g. see FIGS. 3 and 4).

Figure 1:
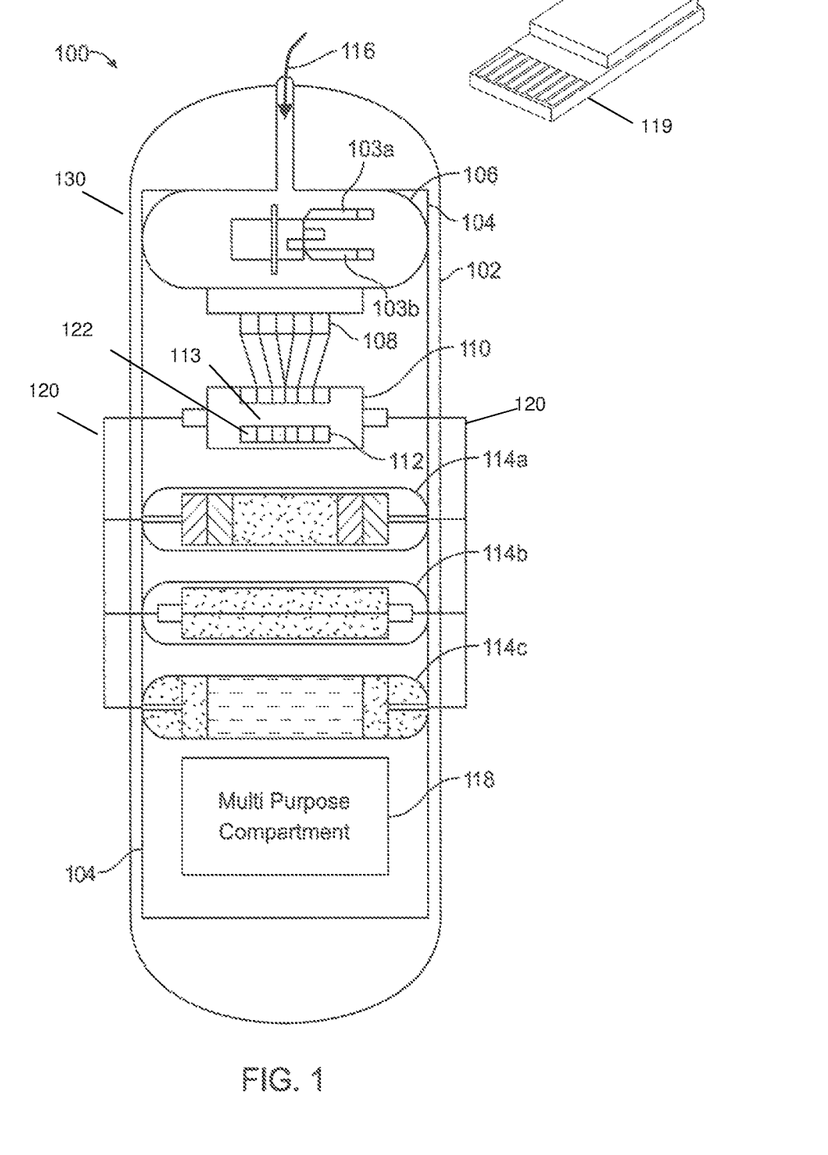
FIG. 1 is a diagram illustrating an exemplary first embodiment of a self-rechargeable bio-fueling micro battery with a balloon nipple diffusion system consistent with the disclosed embodiments for implanting the micro battery into a patient's tissue to power another implanted medical device using the socket system to transfer stored electricity from the micro battery to the medical device.

In another embodiment, the electrodes are entirely encapsulated within the biofuel compartment (e.g. see FIG. 1).

All embodiments of the micro battery comprise at least the biocompatible compartment with an electrode pair, and the glucose biofuel compartment.

The micro battery further comprises at least one microprocessor in communication with the biocompatible compartment through a plurality of connectors that interface with the bio fuel compartment to control the communication between a user mobile device and the bio medical implant device.

The present disclosure further comprises a method of self-recharging a micro battery, and/or supplying electricity to an implanted medical device from the micro battery, comprising the steps of: a) providing a self-rechargeable bio-fueling micro battery comprising a bio-membrane configured to diffuse at least one bio-fluid across an anode electrode and a cathode electrode to generate electron follow for recharging the micro battery and/or for supplying a constant power supply to a connected bio-medical implanted device, whereby the bio-membrane comprises: a biocompatible compartment comprising an anode electrode and a cathode electrode and storing at least one of a chemical substance configured to generate electricity to power the bio-medical implanted device; one or more biofuel compartments configured to store at least one biofuel that is able to generate an electrolyte to create a conductive path for electrons emitted by the anode electrode and the cathode electrode to generate electricity to recharge the micro battery and/or to power the bio-medical implanted device; and a processor in communication with the biocompatible compartment through a plurality of connectors that interface with the biofuel compartment to control the communication between a user mobile device and the biomedical implant device.

The method then comprises diffusing or injecting a biofluid into the biocompatible compartment, wherein the biofluid comprises a biological acid juice comprising at least one of: a lemon juice, an orange juice, a pineapple juice, and a sour juice; and/or an ingested food, and wherein the micro battery is recharged by the biofluids reacting with the anode and cathode electrodes within the bio-compartment to generate electricity.

The method then compromises generating electricity by one or more biofuel cells to recharge the micro battery and/or to power the bio-medical implanted device, wherein the biofuels comprise a blood fuel, a glucose fuel, a microbial fuel, and/or an enzyme fuel; and transferring the generated electricity from the micro battery to the bio-medical implanted device to power said device.

In the micro battery and method of its use, at least one of chemical substance stored in biocompatible compartment comprises acid solutions; and/or a sugar solution including hydrochloric acid, potassium chloride, sodium chloride, sugar, and/or glucose.

The micro battery and its method of use further comprises a balloon nipple extending from the micro battery into the surrounding tissue and connected to the biocompatible compartment.

In the micro battery and method of its use, the compatible compartment is able to be refueled by at least one of: directly swallowing biological acid juices comprising lemon juice, orange juice, pineapple juice, and sour juice; by ingestion of food; by directly refilling the balloon nipple via connecting to three dimensional catheters.

In the micro battery and method of its use, the processor provides plurality of instructions to the one or more bio fuel compartments automatically by an inbuilt memory; and the processor turns on/off automatically by recharging the one or more bio fuels compartments; or the processor turns on the bio membrane and/or the biocompatible compartment in the absence of the availability of fuel in the one or more bio fuel compartments.

The micro battery and its method of use further comprises a tuning capacitor included in the processor that receives power from the one or more bio fuel compartments and transmits it to an authenticated implanted medical device.

The micro battery and its method of use further comprises one or more oral therapies, an intravenous drip, chemical infused patches, and chemical baths are used to infuse a plurality of chemical substances into human body to recharge the micro battery.

The micro battery and its method of use further comprises a glucose monitoring chamber able to measure blood glucose and oxygen levels within a diabetic patient's arterial blood, and/or to burn excess glucose in the blood to reduce or eliminate the need for insulin medication.

The micro battery and its method of use further comprises a no-dialysate micro hemodialysis blood filtering system.

BRIEF DESCRIPTION OF THE DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein:

FIGS. 7A-7D illustrate various views of the blood filter that is functioning as a no-dialysate micro hemodialysis system, which is an additional component of the micro battery.

DETAIL DESCRIPTION OF EXEMPLARY EMBODIMENTS

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof, as well as additional items. The terms "a" and "an" herein do not denote a limitation of quantity, but rather denote the presence of at least one of the referenced items. Further, the use of terms "first", "second", and "third", and the like, herein do not denote any order, quantity, or importance, but rather are used to distinguish one element from another. As used herein, the term "about" refers to plus or minus the stated amount.

Micro Battery with Internal Electrodes

FIG. 1 is a diagram of micro battery 100 illustrating an exemplary preferred embodiment of a self-chargeable bio-fueling micro battery consistent with the disclosed embodiments, wherein the micro battery is swallowed and then adheres to the internal walls of the stomach lining. According to a non-limiting embodiment of the present disclosure, the self-chargeable bio-fueling micro battery 100 is designed in the form a capsule that is analogous in size to the half size of a grain of rice (e.g. about 11.5 millimeters in length). Micro battery 100 is encapsulated in glass or titanium material 102 that is biocompatible, and that includes an enclosure made of polypropylene polymer to prevent the movement of micro battery 100 after placing it inside the user's body. The polymer is also used to hold micro battery 100 in the arranged place by binding with the connective tissue and other kinds of cells around it. For example, in an embodiment, an enclosure comprises a thin layer of polypropylene polymer that is placed over the micro-battery after it is implanted into tissue to prevent it from dislodging. In another embodiment, the closure comprises a thin layer of polypropylene polymer, or other similar biocompatible polymer well known to the skilled artisan, that coats the entire outer surface of the micro battery.

In an embodiment, the micro battery 100 is positioned in between a stomach flesh and intestine flesh to operate bio-medical implant devices, which may include but are not limited to: deep brain neurostimulators, cochlear implants, gastric stimulators, cardiac defibrillators/pacemakers, foot drop implants, insulin pumps, and the like. Also, in an embodiment, the micro battery 102 is surgically placed inside the human body, or swallowed, and is removed surgically.

As shown in FIG. 1, the micro battery 100 includes a bio-membrane 104 that functions to diffuse the power in an active and a passive mode for charging the batteries itself by using the biological fluids. The biological fluids may include, but are not limited to: blood glucose, blood serum, gastric juice, blood, and any body heat and the like. Furthermore, the bio-membrane 104 includes multiple compartments, such as electrodes 103a,b and 114a,b,c and a diffusion system to contact with bio-fluids for producing electricity; and bio-membrane 104 comprises silicon rubber or a diaphragm and the like. The micro battery 100 further includes a cylindrical housing 130 and a diaphragm welded to seal the different compartments of the micro battery 102. Also, in some embodiments, the inner walls (at 104) and/or outer housing 130 of the micro battery 100 can be three-dimensionally shaped, which may include, but is not limited to: a cube, a cuboid, a pyramid, a cone, a hemisphere, and octahedron and the like. The electrodes 130a,b and 114a,b,c are independent from the different compartments of the micro battery 100.

Also, as shown in FIG. 1, in some other embodiments, the micro battery 100 positioned in the human body is made of biocompatible and inert materials in order to prevent or reduce any adverse immunological response to micro battery. In some preferred embodiments, the micro battery 100 is one of voltaic cells that generates electricity on the standard principle of biocompatible compartment 106, which is also referred to as a primary compartment. Biocompatible compartment 106 is configured to store a chemical substance, which may include but is not limited to: an acidic solution or sugar solution mainly including hydrochloric acid, small quantities of potassium chloride and sodium chloride, or sugar/glucose and the like used as the electrolyte. Also, in some embodiments, biocompatible compartment 106 is filled with acid, and a refill electrolyte is supplied through bio membrane 104, which is coupled with a balloon nipple 116 using an external injection device. In some embodiments, the biocompatible compartment 106 is refueled by directly swallowing biological acid juices, which may include but are not limited to: lemon juice, orange juice, pineapple juice, and any other sour juice and the like. The refillable balloon nipple 116 is made of a biocompatible silicon rubber in order to inject the solution externally, and the repeated injections of silicon rubber balloons do not hamper the body. In some other embodiments, the biocompatible compartment 106 is refueled with the biological acid juices through intravenous therapy by infusing the predefined chemical substance into body. Also, in some embodiments, the biocompatible compartment 106 is refueled with the biological acid juices by using at least one skin patch, a foot t bath and the like processes to infuse predefined chemical substances into the body that travel to the micro battery 100, and enter the biocompatible compartment 106, e.g. via diffusing across the nipple 116.

Additionally, bio-membrane 104 is configured to diffuse at least one bio-fluid across the anode electrode and the cathode electrode (103a and 103b) to generate electron follow for recharging the micro battery and/or for supplying power to a connected bio-medical implanted device. Bio-membrane 104 comprises: a biocompatible compartment 106 storing at least one of a chemical substance configured to generate electricity to power the bio-medical implanted device (not shown); and one or more biofuel compartments 114a, 114b and 114c configured to store at least one biofuel for generating an electrolyte to create a conductive path for electrons emitted by the electrodes 103a and 103b.

In one embodiment, at least one electrode pair extends from the micro battery into the surrounding tissue into which the micro battery is implanted (e.g. see FIG. 2-7); and in another embodiment, all electrode pairs do not extend into surrounding tissue and are thus entirely encapsulated within the micro battery housing (e.g. FIG. 1, 130).

Micro battery 100 further comprises at least one microprocessor 110 in communication with the biocompatible compartment 106 through a plurality of connectors 113 that interface with the bio fuel compartments to control the communication between a user mobile device (e.g. see FIG. 4, 430) and the biomedical implant device.

Additionally, in an embodiment, the electricity-power generated by the micro-battery is transferred to an implanted medical device (not shown) via the socket system 119, which connects to power connection ports 108, and to the medical device power connection ports.

Biocompatible Compartment

The biocompatible compartment 106 houses the electrodes 103a and 103b, and is configured to further store the electrolyte that comprises a chemical substance, which may include but is not limited to: an acidic solution or sugar solution mainly including hydrochloric acid, small quantities of potassium chloride and sodium chloride, or sugar/glucose and the like suitable for use as the electrolyte.

The biocompatible compartment 106 can be refilled with the electrolyte that is supplied through the balloon nipple 116 via passive diffusion or actively injecting (e.g. via connecting to a three dimensional catheter); and/or from the biofuel compartments (e.g. FIG. 1, 114a,b,c; and FIG. 2-7, 214a,b,c).

Various method for passive refilling of the electrolyte are envisioned, such as: drinking juices; intravenous injections into the user's circulatory system; skin patches; foot bath and the like processes to infuse predefined chemical substances into the user's blood and circulatory system, that will then pass through via diffusion the balloon nipple 116 material and into the biocompatible compartment 106. For example, the biocompatible compartment 106 is refueled by the user directly swallowing biological acid juices, which may include but are not limited to lemon juice, orange juice, pineapple juice, and any other sour juice and the like.

In an active refilling, the balloon nipple 116 is directly injected with refill electrolyte (e.g. via a syringe or catheter).

In all embodiments, balloon nipple 116 is made of biocompatible material that readily permits diffusion of fluids one-way (e.g. into the micro battery 100, and not out of it), such as silicon rubber material. It is recognized that the skilled artisan would readily know of other similar materials for making the balloon nipple 116.

Electrodes

In some preferred embodiments, the electrodes 103a and 103b that are coupled to the biocompatible compartment 106 are made of platinum (Pt) and zinc (Zn) and are employed as the anode and the cathode. In some other embodiments tantalum (Ta) and carbon are used as cathode and anode, respectively, by considering the biocompatibility and the standard potential of the micro battery 100. In the chemical reactions used for generating electricity, platinum does not dissolve, and zinc dissolves slightly as represented in equations (1).

(1).

The Zn is the essential trace metal and safe for humans; and Pt is safe as well and importantly is active at the reduction of hydrogen ion, which prevents the polarization, a critical issue of a voltaic cell. In some embodiments, the theoretical voltage of the micro battery 100 is calculated as 1.92 V from the standard electrode potential of Pt and Zn, which is greater than that of the conventional voltaic cells utilizing copper and zinc as the anode and the cathode, respectively. In some other embodiments, polydimethylsiloxane (PDMS), which is a thermosetting polymer, is used for the casing as diaphragm membrane materials, which is a biocompatible polymer and has been widely used to form micro structures. This is formed by sandwiching the porous ceramics between the electrodes to filter foreign materials, spread and, more importantly, to hold the gastric fluid. Titanium (Ti) and subsequently Platinum (Pt) are evaporated on a thin glass plate to form the anode. The Ti works as a contact metal to enhance the adhesion of Pt to the glass. The metals cannot be deposited onto PDMS directly since the deposition involves heat and generates cracks in the Pt film on the PDMS. A thin Zn plate is used as the cathode. Fine Porous Ceramics is used as the filter. The electrodes and the filter are sandwiched by the PDMS casing, which are bonded via surface activation by oxygen plasma.

Microprocessor

Also, further as shown in FIG. 1, the biocompatible compartment 106 is electrically connected with a microprocessor 110 through power connection ports 108. The processor 110 positioned in the micro battery 102 is micronized in size (e.g. a microprocessor), and it transmits instructions to the other biological fuels compartments (e.g. 114a, 114b and 114c) automatically. The processor 110 includes a wireless transceiver 112 and a global positioning system chip 113 for receiving GPS signals to locate/track the micro battery 100. The wireless transceiver 112 is used to receive data from and transmit data to the authenticated user electronic computing devices outside the body, where the device may include but is not limited to a smartphone, tablet, laptop, desktop, PDA, or any electronic equipment and the like used to operate the bio-medical implants.

Communication between the micro battery and the user electronic computing device (e.g. FIG. 4, 430) to monitor the battery and the power to the implanted device is accomplished via a variety of means. For example, the transceiver 112 of the processor collects the global positioning system chip information and transmits it to the electronic computing device; or radio signals transmitted to the portable device 430 with a unique identification number; or a mobile application 444 is downloaded in the portable device interprets the radio signals and displays the code number and translates the code to a message; or the transceiver establishes a wireless communication with a portable device through plurality of wireless communication technologies well known in the art.

The mobile application 444 comprises one or more non-transitory computer-readable storage media having computer-executable instructions stored thereon which, when executed by one or more computers, cause the one or more computers to perform operations to, e.g. receive and display the amount of electricity produced in the micro battery for a set period of time by each pair of electrodes and/or the whole micro battery, and/or the amount of electricity/power remaining in the micro battery and/or the implanted medical device.

In some preferred embodiments, the processor 110 performs multiple functions within the micro battery 100. The multiple functions may include but are not limited to updating, storing and executing operations and applications and the like. The processor 110 also includes a memory 122 and other necessary features to perform the abovementioned functionalities. In some preferred embodiments, the processor 110 and transceiver 112 may work in conjunction for external technological communication through satellite. The processor 110 can control communications transmitted and process communications received through transceiver 112, and such transmissions may include instructions to processor 110 or data sent by processor 110. The wireless transceiver 112 transmits the data to the externally placed user electronic computing devices (e.g. a portable device with cellular or internet connectivity). In some embodiments, the processor 110 can turn off-on on the compartments of micro battery 102 at certain intervals to ensure constant power, externally/remotely.

In some other preferred embodiments, the actual processor 110 placed inside the micro battery 100 holds the important information, as well as a tuning capacitor and an antenna coil. The capacitor receives power and transmits it to the user electronic computing device downloaded with the specific software application for the micro battery 100 and/or the medical device that it powers. The microchip's information can then be picked up through the antenna, which is a copper coil. The micro battery 100 transmits radio signals to the portable device with the authenticated identification number. The software application can then interpret the radio waves and display the code number and translate the displayed code as a message to the user.

The micro battery processor provides plurality of instructions to the one or more bio fuel compartments automatically by an inbuilt memory. And the processor turns on/off automatically by recharging the one or more bio fuels compartments, or the processor turns on the bio membrane in the absence of the availability of fuel in the one or more bio fuel compartments. And a tuning capacitor (inside 607 of FIG. 6) included in the processor receives power from the one or more bio fuel compartments and transmits it to authenticated mobile electronic computing devices.

Biofuel Compartments

Additionally, in FIG. 1, the micro battery 100 includes one or more biofuel compartments 114a, 114b and 114c that are connected via wires 120. The biofuel compartments are used to store their respective bio-fuels such as blood fuel, glucose fuel, microbial fuel and the like for generating electrolyte and to create a conductive path for electrons emitted by electrodes within each compartment 114a, 114b and 114c. In some embodiments, the bio fuel compartment may include a blood fuel cell 114a used to generate electrolyte by the blood. In some embodiments, the bio fuel compartment may include additionally, or alternatively, a glucose fuel 114b used to generate electrolyte by the glucose included in the body fluid. In some other embodiments, the biofuel compartment may include additionally, or alternatively, a microbial fuel compartment 114c used to generate electrolyte by producing microbial fuel using intestinal micro-organisms to convert bio-convertible substrates directly into electricity.

Also, in some embodiments, the biofuel compartment 114b further comprises a platinum catalyst that strips electrons from the glucose, mimicking the activity of cellular enzymes that break down glucose to generate ATP, the cell's energy currency. The biofuel compartments 114a, 114b and 114c can generate power up to hundreds of microwatts enough to power an ultra-low-power and clinical implant.

Multipurpose Compartment

Additionally, the micro battery 100 may further comprise a multipurpose compartment 118 used as a medical implant device, or a drug reservoir or any other circuit positioned to connect with general electrical mechanisms. Compartment 118 can be about 0.5 millimeters to about 2 millimeters in size.

For example, compartment 118 can store drugs for delayed time release, such as contraceptive drug implants comprising Norplant®, Implanon®, and Nexplanon®, birth control pill and nicotine and Insulin pumps for Type 1 diabetics, bipolar disorder and schizophrenia too. FDA approved a Nexplanon-like implant called Probuphine®, meant to deliver a controlled dose of buprenorphine over a period of six months. This approach is suitable for long-term medication.

See FIGS. 6 and 701 to 707 for specific embodiments of systems inserted into compartment 118.

Micro Battery with External Electrodes Extending into Tissue

Figure 2:
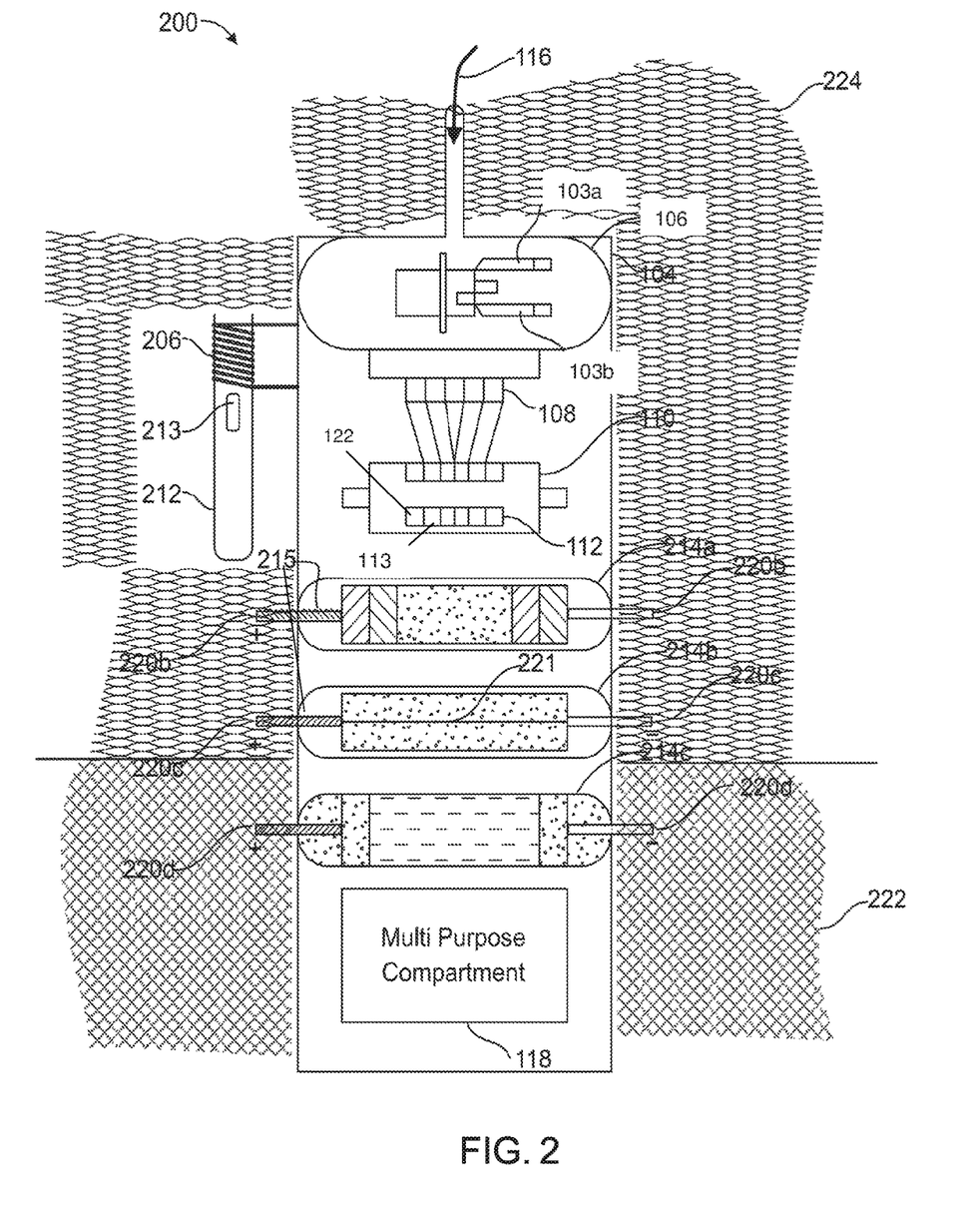
FIG. 2 is a diagram of a second embodiment of the self-rechargeable bio-fueling micro battery without an external housing or closed container, and comprising electrodes that extend from the biofuel compartments into surrounding tissue comprising: stomach, intestine, and arterial tissue.

FIG. 2 is a diagram of another embodiment of a micro battery 200 comprising a plurality of compartments used to generate power from the different body fluids collected in the specific compartments (106 fruit juices, 214a blood, 214b glucose, 214c microbes). As illustrated, the micro battery 200 is surgically implanted in the human body and positioned between the stomach flesh 224 and intestine flesh 222. It is noted, though, that one of skill in the art would readily know of other positions of the micro battery 200 in surrounding tissue comprising: stomach, intestine, and arterial tissue, through swallowing and/or through surgical implantation.

As shown in FIG. 2, the biocompatible membrane 106 is configured to store a chemical substance, which may include but is not limited to: an acidic solution or sugar solution mainly including hydrochloric acid; small quantities of potassium chloride and sodium chloride; or sugar/glucose and the like used as the electrolyte. Also, in some embodiments, the biocompatible compartment 106 is filled with acid, and a refill electrolyte is supplied through bio membrane 106 coupled with balloon nipple 116 using an external injection device (not shown). In some embodiments, the biocompatible compartment 106 is refueled by directly swallowing biological acid juices, which may include but are not limited to a lemon juice, orange juice, pineapple juice, and any other sour juice and the like. Wires connecting the micro battery 200 to an implanted device may reside under the biocompatible layer of the micro battery, or be welded into it, or the socket system 119 of FIG. 1 is used to transfer power.

Also, as shown in FIG. 2, in some embodiments, a blood fuel compartment 214a is included in the bio-membrane to recharge the micro battery by itself from the blood stream. In this current process, the body heat is used as a power source for the micro battery 200 and further used as a power supply for the entire body. As the body temperature differs in different places of the body, the biocompatible compartment 106 of the micro battery provides a power backup to maintain the constant power supply through the instruction of the processor 112 controlled by the portable device software application (FIG. 4, 444). In some embodiments, an energy gradient provides the power flow to the compartments 214a, 214b, and 214c of the micro battery. Also, in some embodiments, in case of blood clots or arteriosclerosis, the micro battery may not receive the required power and in some cases, if anything blocks the electrodes to access the blood, then also the power cannot be generated. Thus, in such cases the biocompatible compartment 106 (e.g. voltaic/acidic cell) works as a backup and the micro battery receives power from the current flow between electrodes 220b. In biofuel compartments, the power is generated by causing a chemical reaction at a controlled rate and by burning blood chemicals from blood cells of the human body. The electrodes 220b of the blood fuel compartment 214a is coupled with flesh of the stomach to create a conductive path for the electrons emitted by the electrodes 220b for operating the bio-medical implant devices (not shown).

Further as shown in FIG. 2, in some embodiments, glucose-fuel compartment 214b of the micro battery consists of two electrodes 220c, anode (−) and cathode (+). The anode is coated by a mediator comprising a sugar digesting enzyme layer. The cathode also has an analogous construction, but in the present disclosure the mediator 215 is covered by oxygen reducing enzymes. The electrodes 220c of the glucose fuel compartment 214b are coupled at the flesh of the stomach to create a conductive path of electrons emitted by the electrodes for operating the bio-medical implants. The two electrodes of 220c are placed on either side of a cellophane separator 221. The enzymes at the anode break down glucose molecules into gluconolactone, hydrogen and electrons.

Glucose Gluconolactone+2H++2e−

The hydrogen ions move towards the cathode through the separator 221 while the electrons follow the external path through the stomach skin (conductor) to reach the cathode of 220c. The enzymes at the cathode reduce oxygen with the electrons causing it to combine with the hydrogen ions to form water.

$$O_2 + 4H^+ + 4e^- = 2H_2O$$

Thus, the movement of electrons (current) generates a voltage across the load for further producing power, which is used to recharge the micro battery 200 and/or power the implant device. It could be medically important to note that these reactions can take place in a neutral solution because enzymes are selective in nature. There is no cross reaction between the two electrodes of 220c, which is unlike in the processes that occur in the biocompatible compartment 106 using lemon juice as a chemical substance. The enzymes and mediators coating the electrodes 220c are held in place by cross-linked enzyme clusters on carbon nanotubes. The hydrogen ions will still find their way to the cathode. In some embodiments, the glucose fuel compartment including sugar has an energy storage density of 596 amp-hours per kilo higher than lithium-ion batteries. This fuel compartment 214b is refillable with a solution of maltodextrin, and generates the by-products of electricity and water.

Also, further as shown in FIG. 2, in some embodiments, microbial fuel compartment 214c included in the micro battery uses micro-organisms to transform bio convertible substrates directly into electricity. The bacterium in the micro-organisms is used as the anode, and the electrons flow from the cathode through a resistor (not shown). The anode and cathode of the electrode 220d are positioned at the intestine flesh 222 (e.g. into the intestinal wall enough to access the microbes residing therein). The catalytic actions of the micro-organisms have been used to produce electrical output from the different carbohydrates and complex substrates.

In above mentioned glucose fuel compartment 214b, the power output produced is in the range of about 50 μW, which is sufficient to supply a cardiac pacemaker. Both glucose and oxygen are present in the compartment 214b, and in the tissue of all eukaryotic organisms, which may include but are not limited to human beings. The fuel compartment receives the support from the body's own resources, which may include but is not limited to the metabolic properties of living cells and the like to generate enough energy for powering an array of clinical implant devices, including drug delivery systems, diagnostic tools, and human augmentation devices and the like. Also, the catalytic reactions of microorganisms produce electrical output from different carbohydrates and complex substrates up to 50 uW range sufficient to run a pacemaker.

Though not depicted in FIG. 2, in some embodiments, enzyme fueled compartments included in the micro battery utilize the motor enzymes, which may include but are not limited to: inesin, RNA polymerase, myosin, and adenosine tri-phosphate (ATP) synapse and the like. The motor enzymes are fueled by the ATP molecule, including adenine, ribose, and three phosphate groups that are linked by covalent bonds. Among the three phosphate groups, the first phosphate group signaled by the coenzyme is removed, and a large amount of energy is released in the form of a reaction product called adenosine diphosphate (ADP). Thus, in a further requirement of energy, the second phosphate group is released to create adenosine monophosphate (AMP). The energy created is made available to be used for chemosynthesis, locomotion (including muscle contraction in animals), and the active transport of ions and molecules across cell membranes. Thus, the ATP molecule is refueled by the re-phosphorylation of ADP and AMP using the chemical energy generated from the oxidation of food and used to recharge micro battery fuels.

Also, further as shown in FIGS. 2 and 4, a wireless transceiver 212 comprises a light emitting diode (LED) 213 coupled with the biocompatible compartment 106 and/or the biofuel compartment 214a through an antenna coil 206 to transmit and receive data from the any of the user's electronic computing devices, e.g. a mobile device 430 comprising the mobile application 444 of the present invention, or the like. The mobile device may include but is not limited smartphone, PDA, tablet, laptop, and any other mobile device and the like with internet connectivity.

Micro Battery with Internal and External Electrodes

FIGS. 3 and 4 is a diagram illustrating a closed container 300 housing a self-rechargeable bio-fueling micro battery, e.g. per FIG. 2, that is implanted in the stomach lining of a human body; and with a nipple 116 extending from the top end of the container for refilling of the biocompatible compartment 106. Container 300 comprises at a minimum: the biocompatible compartment 106 with the electrode pair 203a,b, and at least a glucose biofuel compartment 214a.

FIGS. 3 and 4 depict all three biofuel compartments (214a,b,c) with electrode pairs 220b, 220c, 220d) extending from opposing container sides through holes 250. FIGS. 3 and 4 further depict an alternative embodiment of electrode pair 203a,b, extending from the housing 300 at opposing sides. . . . Other embodiments are envisioned within the scope of the invention, such as a micro battery with one, two, or three biofuel compartments, where the glucose compartment 214b is required; and/or where the electrode pairs (103a,b; and, 220b,c,d) extend from the same container side, aligned in parallel at a few millimeters distance apart (e.g. about 1-5 millimeters) as depicted in FIGS. 1 and 2.

The biocompatible micro battery is placed inside of container 300 and positioned in any part of the human body. For example, in FIG. 3, the disclosure depicts the positioning of the container 300 in the stomach lining to which the internal flesh and the interior of the external flesh 324 is surrounded. Also, electrodes 203a,b and 220a,b,c of FIGS. 3 and 4 extend from container holes 250 on opposing sides of the container, and connect with the external flesh 324 of the stomach. The connected electrodes receive the power generated by at least one biofuel compartments (e.g. see 214 a, 214b, and/or 214c) included in the micro battery and creates a conductive path of electrons emitted by the electrodes for operating the bio-medical implant devices.

As shown in FIG. 3, the different fuel compartments included in the micro battery acts according to their necessity. For example, in case of the unavailability of the required amount of glucose in the body levels of the glucose fuel compartment 214b, the micro battery receives power from the any other compartment, such a microbial fuel compartment or blood fuel compartment (214a, 214c). Similarly, in the unavailability of fuel in any one of the three compartments, one or the other compartment is activated to generate power and recharge the micro battery by itself and operate the bio-medical implant devices.

FIG. 4 is a diagram illustrating the container 300 of FIG. 3 housing the micro battery, and establishing a wireless communication with a user's portable device (e.g. smartphone 430 with mobile application 444 of the present invention that is installed thereon). According to a non-limiting exemplary preferred embodiment of the present disclosure, the micro battery is placed inside a container 300 and is positioned in any part of the human body (e.g. surgically or via swallowing), per FIG. 3. The micro battery establishes a wireless communication via a wireless network 432 with an electronic computing device 430, which may include but is not limited to a smartphone, PDA, laptop, tablet and any other portable device and the like with internet connectivity and the mobile application of the present invention installed thereon to remotely monitor the micro battery, and/or a third party mobile application to monitor the implanted medical device.

As mentioned in above FIG. 1, in some embodiments the wireless transceiver 112 that is positioned in the micro battery is used to transmit and receive data from the portable device 430. For convenience the present disclosure is depicting only a mobile device 430 for communication. However, it should be understood that in general there may be any other electronic computing devices, such as a laptop, desktop, tablet, and the like used as similar as the mobile device 430. Therefore, the present disclosure is not limited to the usage of mobile device for establishing a communication with the micro battery, as long as it has the capacity to communicate wirelessly with the transmitter of the micro battery (e.g. RFID, Zig bee, Wi-fi, Li-Fi, Bluetooth, and the like).

Method of Use

Figure 5:
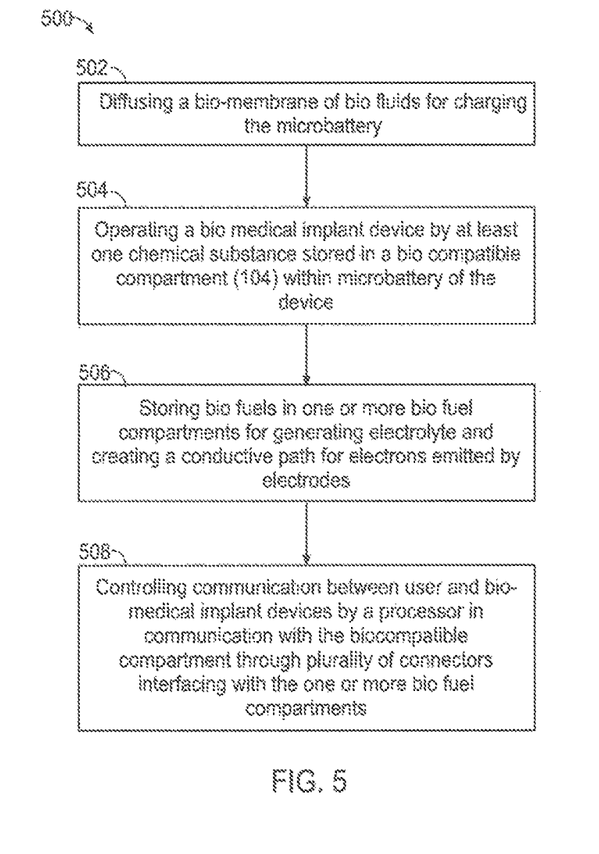
FIG. 5 is a flowchart of micro battery steps illustrating an exemplary method of use of a self-chargeable bio-fueling micro battery.

FIG. 5 is a flowchart 500 of computer steps illustrating an exemplary method of use of the self-rechargeable bio-fueling micro battery. According to an embodiment of the present disclosure, the method of self-charging the micro battery starts at step 502 by diffusing a bio-membrane with at least one biofluid for recharging the micro battery and/or powering the implant device to which it is connected. The biofluids may include but are not limited to blood glucose, blood serum, gastric juice, blood and any body heat and the like, which may diffuse into the micro battery via a balloon nipple (e.g. FIG. 1, 116). Additionally, or alternatively, the nipple 116 can be injected with the biofluid (e.g. via a catheter).

As shown in FIG. 5, at step 504 at least one bio-medical implant device is powered by at least one chemical substance stored in at least one of biocompatible compartments (e.g. FIGS. 1, 2; blood 214a, glucose 214b, and/or microbe 214c). The chemical substance may include but is not limited to: an acidic solution or sugar solution mainly including hydrochloric acid, small quantities of potassium chloride and sodium chloride, or sugar/glucose and the like used as the electrolyte.

Next at step 506, the bio-fuels stored in multiple bio fuel compartments are used for generating electrolyte and to create a conductive path for electrons emitted by electrodes to generate electricity that re-charges the micro-battery and/or powers the implanted medical device. The bio-fuels may include but not limited to blood fuel, glucose fuel, microbial fuel, enzyme fuel and the like.

Further at step 508, a processor in communication with the biocompatible compartment through a plurality of connectors interfaces with the multiple biofuel compartments, and the processor is used to control communication between the user authenticated portable device and a bio medical implant device within the user.

Glucose Measuring System

Figure 6:
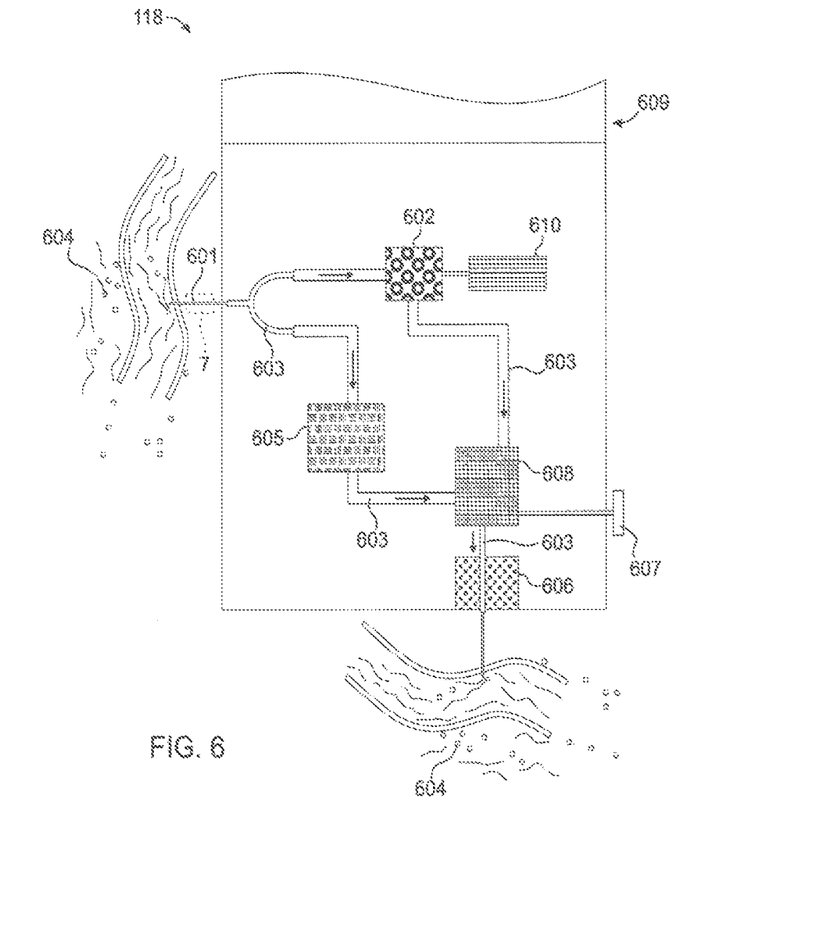
FIG. 6 is a diagram illustrating an exemplary embodiment of a glucose burning chamber housed within the multipurpose compartment of FIG. 1, for measuring glucose and oxygen levels within the arterial blood of a diabetic patient.

FIG. 6 is a diagram of a glucose measuring system 609 comprising a glucose burning chamber housed within the multipurpose compartment of FIG. 1, for measuring glucose, and oxygen levels within the arterial blood of a diabetic patient who has a micro battery 100.

As shown in FIG. 6, system 609 is housed within the multipurpose compartment 118 of FIG. 1.

The glucose system 609 works on the same principle as an oxidation of glucose, catalyzed by the enzyme glucoseoxidase in situ; and it can detect and measure glucose from the blood.

Hollow tube 601 extends out from compartment 118 and micro battery 100 outer housing, and into the user's artery/cell/tissue, and draws glucose 604 via diffusion from the blood into the glucose system 609. The diffused glucose then reacts with oxygen electrode 602, catalyzed by the enzyme glucoseoxidase and a potentiostat 610 to control the voltage difference between a working electrode and a reference electrode (not shown). Both electrodes are contained in an electrochemical cell (not shown). The potentiostat implements this control by injecting current into the cell through an auxiliary or counter electrode to measure the current flow between the working and counter electrode. Oxygen concentration is determined by the oxygen electrode 602, which functions independent of the blood/tissue oxygen concentration; and the re-circulating enzyme solution is allowed to equilibrate with the environmental oxygen concentration before reuse. Polysulfone hollow fiber membranes, with an internal diameter 0.5 mm, outer diameter 0.8 mm, length 5 cm, are used for the collection of blood passing through the system 609.

System 609 further comprises a micro-dialysis system to remove access glucose from the blood of a diabetic patient, wherein the system comprises: an enzyme reservoir 605; a filtrate collector 608; charcoal samples 606; and light emitting diode 607.

Hollow fiber tube 601 is inserted into the artery, and on both ends to polyethylene connecting tubes (pe-tube 603), with e.g. an internal diameter 0.4 mm, and an outer diameter 0.8 mm. One end of each connecting tube is sealed tightly.

Diffused blood passes through tube 603 and through the reservoir 605 containing the enzyme that reacts with the blood.

Filtrate collector 608 combines the blood from 605 and 602 and passes it through the charcoal filtration at 606 to remove excess glucose and other blood components known to filter out of a patient's blood during dialysis. The cleaned blood is then passed back into the user's circulatory system.

The Light emitting diode (LED) 607 is used to test whether the battery is working to produce electricity (e.g. before implantation the user can test the battery to see if it is working, as indicated by the LED turning on).

Blood Filter System

FIG. 7 is a detailed view of the blood filter in FIG. 6, 601. This blood filter technology 601 (FIG. 7) is a no-dialysate micro hemodialysis system with water permeability of the dialysis membrane. No-dialysate micro hemodialysis systems allow miniaturization of the hemodialysis system, which is an implantable dialysis system comprises a "biofuel micro battery" body as disclosed herein. This micro-hemodialysis filter 601 contains nano and micro porosity of a poly-ether-sulfone (PES) membrane and water-permeable dialysis membrane. This filter system is composed of micro channels and nano-porous PES membranes that selectively allows low molecular weight molecules to diffuse from blood to dialysis fluid. Blood could be passed into the filter 601 by blood pressure itself. The inlet and outlet of the multilayered filter is connected to the artery and vein, respectively. In this system, the dialysis membrane allows water along with low molecular weight ions to permeate through the membrane. The biofuel micro battery will contain multiple blood filtration system according to filtering need.

Figure 7A:
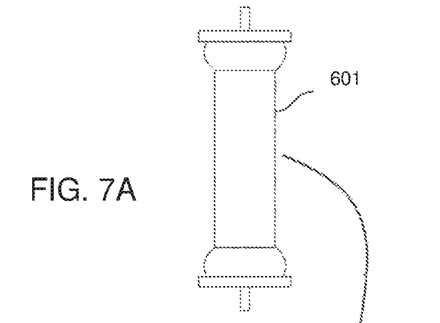
FIG. 7A is a side view of the hollow filter 601 of FIG. 6.

FIGS. 7A-7D illustrate various views of the blood filter that is functioning as a no-dialysate micro hemodialysis system, which is an additional component of the micro battery FIG. 7A is a side view of the hollow filter 601 of FIG. 6, which comprises a diameter of about 0.2 millimeters to about 5 millimeters, wherein "about" refers to 5% plus or minus the stated amount.

Figure 7B:
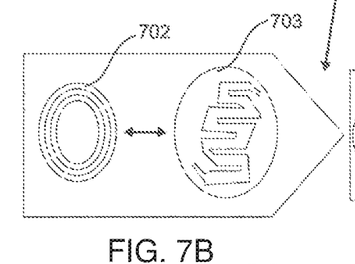
FIG. 7B is an exploded view of FIG. 7A, with the multilayered filter 702, and a horizontal cross-sectional view 703 of the filter showing the multiple layer of PES membranes used to filter the indrawn blood.

FIG. 7B is an exploded view of FIG. 7A, with the multilayered filter 702, and a horizontal cross-sectional view 703 of the filter showing the multiple layer of PES membranes used to filter the indrawn blood.

Figure 7C:
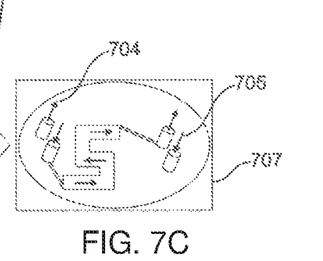
FIG. 7C is an exploded view of one filter layer illustrating blood flow into and out of each filter layer.
Figure 7D:
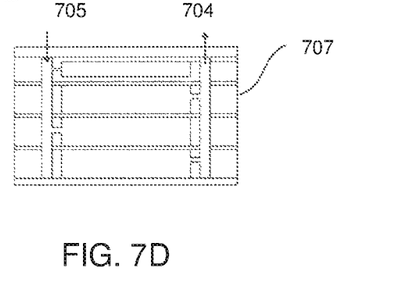
FIG. 7D is a side view of the multiple layers of FIG. 7C.

FIG. 7C is an exploded view of one filter layer illustrating blood flow into 705 and out 704 of each filter layer 707. FIG. 7D is a side view of the multiple layers of FIG. 7C.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

The product names used in this document are for identification purposes only. All trademarks and registered trademarks are the property of their respective owners.

What is claimed is:

1. A self-rechargeable bio-fueling micro battery, comprising:
   a bio-membrane configured to diffuse at least one bio-fluid across an anode electrode and a cathode electrode to generate electron follow for recharging the micro battery and/or for supplying a constant power supply to a connected bio-medical implanted device, whereby the bio-membrane comprises:
      a biocompatible compartment comprising an anode electrode and a cathode electrode, and storing at least one of a chemical substance configured to generate electricity to power the bio-medical implanted device;
      one or more biofuel compartments configured to store at least one biofuel that is able to generate an electrolyte to create a conductive path for electrons emitted by the anode electrode and the cathode electrode to generate electricity to recharge the micro battery and/or to power the bio-medical implanted device;
      a processor in communication with the biocompatible compartment through a plurality of connectors that interface with the biofuel compartment to control the communication between a user mobile electronic computing device and the biomedical implant device; and
      a balloon nipple extending from the micro battery into a surrounding tissue into which the micro battery is implanted and connected to the biocompatible compartment, and able to diffuse or be injected with the bio-fluid.

2. The micro-battery of claim 1, wherein the anode electrode and the cathode electrode form at least one bio-fuel compartment that is configured to extend into the surrounding tissue into which the micro battery is implanted.

3. The micro battery of claim 1, further comprising a wireless transceiver and/or a global positioning system, the micro-battery processor and the transceiver enabled for receiving global positioning system signals to locate and track the micro battery, and to receive data from and adjust settings in the micro battery.

4. The micro battery of claim 1, wherein the one or more biofuel compartments are separated by a biological membrane used for sealing the biofuel compartment and that comprises a silicon rubber, and diaphragm; and/or wherein the micro battery is encapsulated in a glass or titanium material that is biocompatible.

5. The micro battery of claim 1, comprising a glucose fuel cell.

6. The micro battery of claim 5, further comprising a blood fuel cell, and/or a microbial fuel cell, positioned to receive electrolyte from the abdomen and microbes from the intestine to form a bio-fuel that is converted into electrical energy to power an implanted medical device.

7. The micro battery of claim 1, wherein the at least one of chemical substance stored in biocompatible compartment comprises acid solutions; and/or a sugar solution including hydrochloric acid, potassium chloride, sodium chloride, sugar, and/or glucose.

8. The micro battery of claim 7, wherein the biocompatible compartment is able to be refueled by at least one of: directly swallowing biological acid juices comprising lemon juice, orange juice, pineapple juice, and sour juice; by ingestion of food; by directly refilling the balloon nipple via connecting to three dimensional catheters.

9. The micro battery of claim 1, wherein the processor provides plurality of instructions to the one or more bio fuel compartments automatically by an inbuilt memory; and the processor turns on/off automatically by recharging the one or more bio fuels compartments; or the processor turns on the bio membrane and/or the biocompatible compartment in the absence of the availability of fuel in the one or more bio fuel compartments.

10. The micro battery of claim 1, further comprising a tuning capacitor included in the processor that receives power from the one or more bio fuel compartments and transmits it to an authenticated implanted medical device.

11. The micro battery of claim 1, wherein one or more oral therapies, an intravenous drip, chemical infused patches, and chemical baths are used to infuse a plurality of chemical substances into human body to recharge the micro battery.

12. The micro battery of claim 1, further comprising a glucose monitoring chamber able to measure blood glucose and oxygen levels within a diabetic patient's arterial blood, and/or to burn excess glucose in the blood to reduce or eliminate the need for insulin medication.

13. The micro battery of claim 1, further comprising a no-dialysate micro hemodialysis blood filtering system, wherein the system comprises: an enzyme reservoir; a filtrate collector; charcoal samples; and light emitting diode.

14. A method of self-recharging a micro battery, and/or supplying electricity to an implanted medical device from the micro battery, comprising the steps of:
   a) providing a self-rechargeable bio-fueling micro battery comprising
      a bio-membrane configured to diffuse at least one bio-fluid across an anode electrode and a cathode electrode to generate electron follow for recharging the micro battery and/or for supplying a constant power supply to a connected bio-medical implanted device, whereby the bio-membrane comprises:
- a biocompatible compartment comprising an anode electrode and a cathode electrode and storing at least one of a chemical substance configured to generate electricity to power the bio-medical implanted device;
- one or more biofuel compartments configured to store at least one biofuel that is able to generate an electrolyte to create a conductive path for electrons emitted by the anode electrode and the cathode electrode to generate electricity to recharge the micro battery and/or to power the bio-medical implanted device;
- a processor in communication with the biocompatible compartment through a plurality of connectors that interface with the biofuel compartment to control the communication between a user mobile device and the biomedical implant device;
- a balloon nipple extending from the micro battery into a surrounding tissue into which the micro battery is implanted and connected to the biocompatible compartment, and able to diffuse or be injected with the bio-fluid;

b) diffusing or injecting a biofluid into the biocompatible compartment, wherein the biofluid comprises a biological acid juice comprising at least one of: a lemon juice, an orange juice, a pineapple juice, and a sour juice; and/or an ingested food, and wherein the micro battery is recharged by the biofluids reacting with the anode and cathode electrodes within the bio-compartment to generate electricity;

c) generating electricity by one or more biofuel cells to recharge the micro battery and/or to power the bio-medical implanted device, wherein the biofuels comprise a blood fuel, a glucose fuel, a microbial fuel, and/or an enzyme fuel; and d) transferring the generated electricity from the micro battery to the bio-medical implanted device to power said device.

15. The method of claim 14, wherein the at least one of chemical substance stored in biocompatible compartment comprises acid solutions; and/or a sugar solution including hydrochloric acid, potassium chloride, sodium chloride, sugar, and/or glucose.

16. The method of claim 14, wherein the processor provides a plurality of instructions to the one or more bio fuel compartments automatically by an inbuilt memory; and the processor turns on/off automatically by recharging the one or more bio fuels compartments; or the processor turns on the bio membrane and/or the biocompatible compartment in the absence of the availability of fuel in the one or more bio fuel compartments.

17. The method of claim 14, wherein the anode electrode and the cathode electrode form at least one bio-fuel compartment that extends into the surrounding tissue into which the micro battery is implanted.

18. The method of claim 14, wherein the micro battery further comprises a wireless transceiver and/or a global positioning system, positioned to utilize the micro-battery processor and the transceiver for receiving global positioning system signals to locate and track the micro battery, and to receive data from and adjust settings in the micro battery.

\* \* \* \* \*